United States Patent [19]

Kaieda et al.

[11] Patent Number: 4,769,492

[45] Date of Patent: Sep. 6, 1988

[54] METHOD FOR PRODUCTION OF 2,3,4,5-TETRAFLUOROBENZOIC ACID

[75] Inventors: Osamu Kaieda, Osaka; Isao Okitaka, Sakai; Toshiaki Nakamura, Osaka; Koichi Hirota, Suita, all of Japan

[73] Assignee: Nippon Shokubai Kagaku Kogyo Co., Ltd., Osaka, Japan

[21] Appl. No.: 837,549

[22] Filed: Mar. 7, 1986

[30] Foreign Application Priority Data

Mar. 13, 1985 [JP] Japan .................................. 60-48355
Jan. 30, 1986 [JP] Japan .................................. 61-16787

[51] Int. Cl.$^4$ ............................................. C07C 51/38
[52] U.S. Cl. ................................................ 562/479
[58] Field of Search ......................................... 562/479

[56] References Cited

U.S. PATENT DOCUMENTS 3,150,163 9/1964 Plummer ............................ 260/465

FOREIGN PATENT DOCUMENTS 1280596 12/1962 France .

OTHER PUBLICATIONS

Yakobson, Chem. Abst., 64: 12124h (1966).
Kirk–Othmer, Encyclopedia of Chemical Technology, Supp., 1971, pp. 590–598.

Primary Examiner—Michael L. Shippen
Attorney, Agent, or Firm—Omri M. Behr

[57] ABSTRACT

A method for the production of 2,3,4,5-tetrafluorobenzoic acid, which comprises effecting said production by decarbonating 3,4,5,6-tetrafluorophthalic acid in an aqueous medium adjusted to a pH in the range of 0.7 to 2.2 at a temperature in the range of 100° to 220° C.

21 Claims, No Drawings

METHOD FOR PRODUCTION OF 2,3,4,5-TETRAFLUOROBENZOIC ACID

BACKGROUND OF THE INVENTION

1. Field of the Invention

This invention relates to a method for the production of 2,3,4,5-tetrafluorobenzoic acid. More particularly, this invention relates to a novel method for producing 2,3,4,5-tetrafluorobenzoic acid in a high yield by decarboxylating 3,4,5,6-tetrafluorophthalic acid in an aqueous medium.

2. Description of Prior Art 2,3,4,5-Tetrafluorobenzoic acid is a compound useful as an intermediate for medicines and agricultural pesticides. Numerous techniques have been proposed to date for the decarboxylation of phthalic acid derivatives in an aqueous medium [such as in Chemical Abstracts 41, 2083d-(1947) and U.S. Pat. No. 1,939,212, for example]. These techniques are invariably aimed at obtaining unsubstituted benzoic acid. This invention effects as does none of the aforementioned conventional techniques efficient decarboxylation of 3,4,5,6-tetrafluorophthalic acid which is a phthalic acid substituted by fluorine atoms. It has been ascertained to us that when any of the conventional techniques is applied without modification to this invention, the reaction gives rise to secondary products in large amounts and fails to produce 2,3,4,5-tetrafluorobenzoic acid in a sufficient yield.

Generally, a very few methods have been recognized as useful for the production of halogenated benzoic acids by the decarboxylation of phthalic acids substituted by halogens. Undeniably, U.S. Pat. No. 2,439,237 discloses effective production of 2,3,4,5-tetrachlorobenzoic acid by heating 3,4,5,6-tetrachlorophthalic anhydride in an alkaline aqueous solution under application of pressure at a temperature of 220° to 280° C. It, however, makes no mention about fluorides.

We have studied the method of the U.S. Pat. No. 2,439,237 to determine whether or not it can be applied to 3,4,5,6-tetrafluorophthalic acid which is the starting material for the present invention. As indicated in a comparative experiment (control), 3,4,5,6-tetrafluorophthalic acid was simply heated in an alkaline aqueous solution in accordance with the method of the U.S. Patent for the purpose of decarbonating the acid. The reaction which ensued mainly gave rise to trifluorophenol having fluorine atoms substituted by hydroxyl groups and failed to produce 2,3,4,5-tetrafluorobenzoic acid selectively. It may be safely concluded that the fluorine atom at the para position of a benzene ring posessing such an electron-attracting group as the —COOH group is more susceptible to the nucleophilic substitution reaction than the chlorine atom at the same position. By the method of the U.S. Pat. No. 2,439,237, therefore, the alkaline substance is believed to form a phenol by substitution of the fluorine atom. It is, accordingly, proper to conclude that the method, when applied to 3,4,5,6-tetrafluorophthalic acid, is liable to induce secondary reactions and is not useful for the decarboxylation aimed at by the present invention. Methods for the decarboxylation of 3,4,5,6-tetrafluorophthalic acid are described in G. G. Yacobson et al, Journal of General Chemistry, 36, No. 1,144 (1966) and British Pat. No. 2,122,190. The former method causes this acid to react in dimethylformamide as a solvent at a temperature of 145° C. This method, however, dose not deserve commercialization because it produce 2,3,4,5-tetrafluorobenzoic acid in low a yield of 44.0 mol %. The latter method causes the acid to react in an organic solvent, and that at a temperature of 200° C. It does not produce any 2,3,4,5-tetrafluorobenzoic acid but barely gives rise to 1,2,3,4,-tetrafluorobenzene in a yield of 0.5%.

An object of this invention, therefore, is to provide a novel method for the production of 2,3,4,5-tetrafluorobenzoic acid.

Another object of this invention is to provide a novel method for producing 2,3,4,5-tetrafluorobenzoic acid in a high yield by the decarboxylation of 3,4,5,6-tetrafluorophthalic acid in an aqueous medium.

SUMMARY OF THE INVENTION

The objects described above are attained by a method for the production of 2,3,4,5-tetrafluorobenzoic acid by the decarboxylation of 3,4,5,6-tetrafluorophthalic acid in an aqueous medium adjusted to a pH in the range of 0.7 to 2.2 at a temperature in the range of 100° to 220° C.

This invention concerns a method which effects the reaction at a pH in the range of 1.2 to 2.0 and at a temperature in the range of 120° to 195° C. This invention also concerns a method which comprises using, as a catalyst for the reaction at least one compound selected from the group consisting of hydroxides, carbonates, bicarbonates, sulfates, organic acid salts, and fluorides of ammonia, alkali metals, and alkaline earth metals; oxides of alkaline earth metals; and organic bases, and sulfates thereof. This invention further concerns a method which comprises using simultaneously at least one compound selected from the group consisting of sulfates of ammonia, alkali metals, alkaline earth metals, and organic bases and at least one compound selected from the group consisting of hydroxides, carbonates, and organic acid salts of alkali metals and alkaline earth metals; oxides of alkaline earth metals; and organic bases as catalyst for the reaction. This invention pertains to a method which comprises using as a catalyst for the reaction 0.01 to 3.0 moles, per mole of 3,4,5,6-tetrafluorophthalic acid, of at least one compound selected from the group consisting of sulfates and fluorides of ammonia, alkali metals, and alkaline earth metals; and sulfates of organic bases. This invention pertains also to a method which comprises using as a catalyst for the reaction 0.01 to 0.4 mole; per mole of 3,4,5,6-tetrafluorophthalic acid, of at least one compoundselected from the group consisting of hydroxides, carbonates, and organic acid salts of ammonia. This invention pertains further to a method which comprises using as a catalyst for the reaction 0.01 to 0.4 mole, per mole of 3,4,5,6-tetrafluorophthalic acid, of at least one compound selected from the group consisting of oxides, hydroxides, carbonates, and organic acid salts of alkaline earth metals. This invention also pertains to a method which comprises using as a catalyst for the reaction 0.002 to 0.1 mole, per mole of 3,4,5,6-tetrafluorophthalic acid, of at least one compound selected from the group consisting of hydroxides, carbonates, and organic acid salts of alkali metals. This invention further pertains to a method which comprises using as a catalyst for the reaction 0.01 to 1.2 moles, per mole of 3,4,5,6-tetrafluorophthalic acid, of at least one compound selected from the group consisting of organic bases. Further, this invention pertains to a method which comprises simultaneously using as catalysts for the reaction 0.01 to 1.5 moles, per mole of 3,4,5,6-tetrafluorophthalic acid, of at least one compound selected from the group consisting of sulfates of ammonia, alkali metals, alkaline earth metals, and organic bases and 0.02 to 0.4 mole, per mole of 3,4,5,6-tetrafluorophthalic acid, of at least one compound selected from the group consisting of oxides, hydroxides, carbonates, and organic acid salts of alkaline earth metals. This invention relates to a method wherein the aqueous medium containing 3,4,5,6-tetrafluorophthalic acid for the decarboxylation has been obtained by hydrolyzing 3,4,5,6-tetrafluorophthalonitrile with an aqueous solution of 30 to 90% by weight of sulfuric acid at a temperature in the range of 100° to 180° C. and the 3,4,5,6-tetrafluorophthlatic acid consequently containing sulfate ion is used in its unmodified form for the decarboxylation. This invention also relates to a method wherein the aforementioned sulfate ion is present in the form of sulfuric acid, ammonium sulfate, or at least one sulfate selected from the group consisting of ammonia, alkaline earth metals, alkali metals, and organic bases resulting from neutralization of sulfuric acid. This invention relates further to a method wherein the alkaline earth metal is calcium or barium, the alkali metal is sodium or potassium, the organic base is quinoline or pyridine, and the organic acid salt is 3,4,5,6-tetrafluorophthalate or 2,3,4,5-tetrafluorobenzoate.

EXPLANATION OF PREFERRED EMBODIMENT

In accordance with this invention, the decarboxylation of 3,4,5,6-tetrafluorophthalic acid is carried out in an aqueous medium adjusted in advance to a pH in the range of 0.7 to 2.2, preferably 1.2 to 2.0, at a temperature in the range of 100° to 220° C., preferably 120° to 195° C. If the pH of the aqueous medium deviates from the range mentioned above, the selectivity of the decarboxylation for 2,3,4,5-tetrafluorobenzoic acid aimed at by the method is insufficient. If the pH deviates the aforementioned range and the reaction temperature exceeds the upper limit of the range mentioned above, the selectivity is still lower. The pH is affected by the concentration of 3,4,5,6-tetrafluorophthalic acid as the starting material, the amount of the catalyst to be used in the reaction, and the concentration of the residual sulfate ion. Thus, the present invention requires to control the main factors mentioned above. Desirably, 3,4,5,6-tetrafluorophthalic acid is added to the reaction system in an amount of 10 to 200 parts by weight, preferably 20 to 120 parts by weight, per 100 parts by weight of the aqueous medium.

In the method of this invention, although the decarboxylation may be carried out in the absence of a catalyst, it is carried out preferably in the presence of a catalyst. The advantage derived from the use of the catalyst in the reaction resides in the fact that since the reaction can be carried out at a lower temperature than the temperature which is normal in the absence of the catalyst, the pressure spontaneously generated during the reaction is proportionally lower and the reaction can be effectively carried out by the use of an autoclave of relatively low pressure resistance without provision of any extra device for the removal of carbon dioxide gas. Thus, the cost for the installation of the autoclave is low. Moreover, since the reaction proceeds effectively at a low temperature, the otherwise inevitable corrosion of the apparatus by the hydrofluoric acid produced during the course of the decarboxylation can be precluded.

This invention requires to use in the reaction thereof, as a catalyst in a catalytic amount, at least one compound selected from the group consisting of hydroxides, carbonates, bicarbonates, sulfates, organic acid salts, and fluorides of ammonia, alkaline earth metals, and alkali metals; oxides of alkaline earth metals; and organic bases, and sulfates thereof. Since this catalyst affects the pH of the reaction system, the proportion of the catalyst to the reactant is desired to be suitably varied depending on the kind of the compound to be selected as the catalyst. Specifically, the proportion of the catalyst per mole of 3,4,5,6-tetrafluorophthalic acid as contained in its specific concentration in the aqueous medium is desired to fall in the range of 0.01 to 3.0 moles, preferably 0.05 to 1.0 mole when the catalyst is selected from the group consisting of sulfates and fluorides of ammonia, alkaline earth metals, and alkali metals, and sulfates of organic bases, in the range of 0.01 to 0.4 mole, preferably 0.05 to 0.25 mole when the catalyst is selected from the group consisting of hydroxide, carbonate, and organic acid salts of ammonia and oxides, hydroxides, carbonates, and organic acid salts of alkaline earth metals, in the range of 0.002 to 0.1 mole, preferably 0.005 to 0.05 mole when the catalyst is selected from the group consisting of hydroxides, carbonates, and organic acid salts of alkali metals, and in the range of 0.01 to 1.2 moles, preferably 0.1 to 0.9 mole when the catalyst is selected from the group of organic bases. When one or more catalysts selected from the group consisting of sulfates and fluorides of ammonia, alkali metals, alkaline earth metals, and organic bases are used in combination, their total amount is desired to fall in the range 0.01 to 1.5 moles, preferably 0.05 to 0.5 mole, per mole of 3,4,5,6-tetrafluorophthalic acid. When one or more catalysts selected from the group of the other catalysts are used in combination with sulfate catalysts, their total amount is desired to fall in the range of 0.001 to 0.4 mole, preferably 0.005 to 0.25 mole, per mole of 3,4,5,6-tetrafluorophthalic acid. The maintenance of the pH of the reaction system in the specified range fixed by this invention can be easily attained and the effect expected of the catalyst can be satisfactorily obtained by faithful observance of the proportion of the catalyst to the reactant.

Typical examples, of the sulfates of ammonia, alkali metals, alkaline earth metals, and organic bases are ammonium sulfate, sodium sulfate, potassium sulfate, rubidium sulfate, cesium sulfate, magnesium sulfate, calcium sulfate, strontium sulfate, barium sulfate, sulfate of pyridine, sulfate of quinoline, and sulfates of organic amines. Among other sulfates cited above, ammonium sulfate, sodium sulfate, potassium sulfate, barium sulfate, sulfate of pyridine, and sulfate of quinoline prove to be particularly desirable.

Typical examples of the fluorides of ammonia, alkali metals, and alkalines earth metals are ammonium fluoride, potassium fluoride, sodium fluoride, magnesium fluoride, calcium fluoride, strontium fluoride, and barium fluoride. Among other fluorides cited above, potassium fluoride and calcium fluoride prove to be particularly desirable because of their ready commercial availability.

Typical examples of the hydroxides, carbonates, and organic acid salts of ammonia are aqua ammonia, ammonium carbonate, ammonium 3,4,5,6-tetrafluorophthalate and ammonium 2,3,4,5-tetrafluorobenzoate. In these compounds, aqua ammonia and ammonium carbonate normally exist in the form of the salts of 3,4,5,6- tetrafluorophthalic acid and resultant 2,3,4,5-tetrafluorobenzoic acid respectively during the course of reaction.

Typical examples of the oxides, hydroxides, carbonates, and organic acid salts of alkaline earth metals are magnesium oxide, magnesium hydroxide, magnesium carbonate, calcium oxide, calcium hydroxide, calcium carbonate, strontium oxide, strontium hydroxide, strontium carbonate, barium oxide, barium hydroxide, barium carbonate, magnesium 3,4,5,6-tetrafluorophthalate, calcium 3,4,5,6-tetrafluorophthalate, strontium 3,4,5,6-tetrafluorophthalate, barium 3,4,5,6-tetrafluorophthalate, magnesium 2,3,4,5-tetrafluorobenzoate, calcium 2,3,4,5-tetrafluorobenzoate, strontium 2,3,4,5-tetrafluorobenzoate, and barium 2,3,4,5-tetrafluorobenzoate. There are times when these compounds are converted into the salts of 3,4,5,6-tetrafluorophthalic acid or resultant 2,3,4,5-tetrafluorobenzoic acid during the course of the reaction and, with the advance of the reaction, converted into carbonates owing the liberation of carbon dioxide gas.

Typical examples of the hydroxides, carbonates, and organic acid salts of alkali metals are sodium hydroxide, sodium carbonate, potassium hydroxide, potassium carbonate, sodium 3,4,5,6-tetrafluorophthalate, potassium 3,4,5,6-tetrafluorophthalate, sodium 2,3,4,5-tetrafluorobenzoate, potassium 2,3,4,5-tetrafluorobenzoate. The hydroxides of alkali metals are generally converted during the course of the reaction into the salts of 3,4,5,6-tetrafluorophthalic acid and 2,3,4,5-tetrafluorobenzoic acid or into carbonates similarly to the aforementioned compounds of alkali metals.

Typical examples of the organic base are organic amines such as quinoline, isoquinoline, pyridine, triethylamine, trimethylamine, di-isopropylamine, piperazine, hexamethylenediamine, and ethylenediamine.

The tetrafluorophthalic acid to be used in the present invention is synthesized, for example, by a procedure which comprises feeding phthalonitrile together with chlorine onto a bed of activated carbon at a temperature in the range of 270° to 350° C. thereby synthesizing tetrachlorophthalonitrile, fluorinating the resultant tetrachlorophthalonitrile by a method (Example 10) indicated U.S. Ser. No. 776,085 thereby synthesizing tetrafluorophthalonitrile, and subjecting the resultant tetrafluorophthalonitrile to hydrolysis.

For the purpose of this invention, this synthesis is desired to be out by heating the tetrafluorophthalonitrile in an aqueous solution of 30 to 90% by weight of sulfuric acid at a temperature in the range of 100° to 180° C. thereby producing the tetrafluorophthalic acid. At the end of the hydrolysis in the aqueous sulfuric acid solution, the 3,4,5,6-tetrafluorophthalic acid consequently precipitated in the reaction mixture is generally separated by filtration from the aqueous medium. The 3,4,5,6-tetrafluorophthalic acid dissolves in a ratio of 85 parts by weight in 100 parts by weight of water at 25° C. The solubility of this acid sharply falls in an acidic aqueous solution. Thus, an attempt to purify the produced acid simply by washing with water proves to be undesirable because it abundantly dissolves into the water to the extent of impairing the yield of the 3,4,5,6-tetrafluorophthalic acid. This invention does not require any such purification of the produced acid consequently containing sulfate ion can be effectively used in its unmodified form for the purpose of the decarboxylation. To be more specific, the sulfate ion may be present in the form of sulfuric acid, ammonium hydrogen sulfate, and ammonium sulfate as contained in the reaction solution under hydrolysis. Since the 3,4,5,6-tetrafluorophthalic acid already contains ammonium sulfate, which is one of the desirable catalysts for the decarboxylation contemplated by this invention, the decarboxylation can be directly carried out on the 3,4,5,6-tetrafluorophthalic acid without any modification at a temperature in the range of 100° to 220° C.

More desirably, the sulfate ions existing in the form of sulfuric acid and ammonium hydrogen sulfate in the product of the hydrolysis are neutralized with aqua ammonia, hydroxide of alkaline earth metals and alkali metals oxides of alkaline earth metals, and organic faces corresponding sulfates which are useful as catalyst. This practice of converting the sulfate ions into the corresponding sulfates useful as catalyst and then subjecting the 3,4,5,6-tetrafluorophthalic acid now containing the sulfates to the decarboxylation proves to be highly advantageous even from the commercial point of view. In the present invention, therefore, these sulfates are desired to be utilized as catalysts for the decarboxylation.

Further, in this invention, it is particularly desirable to use at least one of the sulfates as a catalyst for the decarboxylation and, in addition thereto, to use as a cocatalyst therefor at least one compound selected from the group consisting of hydroxides, carbonates, and organic acid salts of alkali metals and alkaline earth metals and organic bases. Preferably, the sulfate as a catalyst is used in combination with one compound selected from the group consisting of oxides, hydroxides, carbonates, and organic acid salts of alkaline earth metals as a cocatalyst. When the sulfate is utilized in the presence of at least one compound selected from the group consisting of hydroxide, organic acid salts, and carbonates of alkaline earth metals and alkali metals, oxides of alkaline earth metals; and organic bases, it brings about a synergistic effect as a catalyst. Specifically, it serves to enhance the reaction velocity of the 3,4,5,6-tetrafluorophthalic acid and produce the 2,3,4,5-tetrafluorobenzoic acid in an improved yield.

Besides, the hydroxides, organic acid salts, and carbonates of alkaline earth metals and alkali metals; oxides of alkaline earth metals; and organic basis can serve as trapping agents for the corrosive hydrofluoric acid which is by-produced in a small amount during the decarboxylation, depending on the conditions of reaction. For effective coexistence, the proportion of addition of sulfates of ammonia, alkali metals, and an alkaline earth metals is desired to fall in the range of 0.01 to 1.5 moles, preferably 0.05 to 1.0 mole, that of oxides, hydroxides carbonates, organic acid salts of an alkaline earth metals in the range of 0.02 to 0.4 mole, preferably 0.05 to 0.25 moles, that of hydroxides, carbonates, and organic acid salts of alkali metals in the range of 0 to 0.1 mole, preferably 0.005 to 0.05 mole, and that of an organic base in the range of 0 to 1.2 moles preferably 0.1 to 0.9 mole, respectively per mole of 3,4,5,6-tetrafluorophthalic acid. In the case of calcium sulfate, for example satisfactory results are obtained when this compound is present in the range of 0.01 to 1.5 moles, preferably 0.05 to 1.0 mole, per mole of 3,4,5,6-tetrafluorophthalic acid.

The results brought about by the use of the sulfate as a catalyst are further improved by using calcium hydroxide (which exists in the form of calcium hydroxide at the time of its addition to the reaction system and which, during the course of the reaction, is substantially converted into calcium 3,4,5,6-tetrafluorophthalate, calcium 2,3,4,5-tetrafluorobenzoate, or calcium carbonate) in the presence of 0.02 to 0.4 mole, preferably 0.05 to 0.25 mole, per mole of the 3,4,5,6-tetrafluorophthalic acid. In this case, the amount of the cocatalyst is not desired to be very large because it tends to induce formation of trifluorophenol.

When the 2,3,4,5-tetrafluorobenzoic acid entrains the sulfate ion originating in the preceding hydrolysis, the cocatalyst is partially converted into a corresponding sulfate. The proper amount of the cocatalyst to be added, therefore, must be decided in due consideration of the fact just mentioned. In the case of calcium hydroxide, for example, part thereof is converted into calcium sulfate. The calcium which remains after this conversion into the calcium sulfate, therefore, represents the amount of the cocatalyst.

Of course, in this invention, pure 3,4,5,6-tetrafluorophthalic acid which contains no sulfate ion can be used as the raw material for the decarboxylation contemplated by this invention. In this case, the present invention causes the pure 3,4,5,6-tetrafluorophthalic acid to be placed in the aqueous medium containing as a catalyst therein at least one compound selected from the group consisting of sulfates of ammonia, alkali metals, alkaline earth metals, and organic bases and subjected to decarboxylation, optionally in the additional presence of a cocatalyst.

As the cocatalyst in this case, at least one compound selected from the group consisting of such metals as copper, zinc, cadmium, silver, cobalt, and nickel, and oxides, hydroxides, and carbonates of the metals can be used. Among the compounds cited above, powdered copper, cupric oxide, and zinc oxide prove to be particularly desirable. Virtually any of the catalysts generally used for decarboxylation may be adopted as the cocatalyst herein.

In this invention, when the 3,4,5,6-tetrafluorophthalic acid is dissolved or partially dispersed in water and, in the presence of the specific catalyst, subjected to decarboxylation, the reaction temperature is desired to fall in the range of 100° to 220° C., preferably 130° to 180° C.

If the reaction temperature is higher than the upper limit of this range, the 1,2,3,4-tetrafluorobenzene which has already undergone the decarboxylation is liable to be re-formed and, consequently, the 2,3,4,5-tetrafluorobenzoic acid produced in a lowered yield. If the reaction temperature is not more than the lower limit of the range, there ensues the disadvantage that the reaction velocity of decarboxylation is insufficient and the decarboxylation is deficient in productivity. Although the reaction time for the decarboxylation is not specifically limited, it is desired to fall in the range of 2 to 40 hours, preferably 5 to 30 hours.

The carbon dioxide gas which is produced during the course of the decarboxylation may be sequentially withdrawn out of the system by means of a back-pressure valve without interrupting the reaction. Otherwise, the carbon dioxide gas may be kept sealed in the system throughout the entire course of the reaction. In the former case, the spontaneously generated pressure arising from the carbon dioxide gas can be lowered and the spontaneously generated pressure originating in the aqueous medium can be utilized exclusively for the reaction. Since the reaction can be carried out under a low pressure, the capacity of the autoclave to resist pressure and consequently the cost of autoclave are proportionately low. Where the reaction temperature is in the range of 100° to 220° C., therefore, the reaction is advantageously continued by sequentially withdrawing the carbon dioxide gas from the system so as to maintain the spontaneously generated pressure in the range of 0 to 15 kg/cm$^2$·G, preferably 1 to 10 kg/cm$^2$·G throughout the entire course of the reaction. In the latter case, since the carbon dioxide gas is entrapped within the system, the inner pressure of the system increases as the generation of the carbon dioxide gas continues. The final inner pressure of the system is variable with the space ratio of the reaction vessel, the amount of the raw materials filling the reaction vessel, and the concentration of the raw material placed therein. In the present invention, however, no effect of pressure is recognized.

As the reaction medium, water is used advantageously. Optionally, the aqueous medium may incorporate therein an organic solvent selected from the group consisting of alcohols such as methanol, ethanol, isopropanol, and butanol, glycols such as ethylene glycol and propylene glycol, and dimethylformamide.

After completion of the reaction, when an alkaline earth metal compound has been used as the catalyst, for example, the produced 2,3,4,5-tetrafluorobenzoic acid can be obtained by neutralizing the alkaline earth metal compound wholly into a corresponding sulfate with an aqueous sulfuric acid solution, then hot filtering the reaction solution at a temperature exceeding the level at which the 2,3,4,5-tetrafluorobenzoic acid is precipitated thereby expelling the sulfate from the reaction solution, and thereafter cooling the filtrate to room temperature thereby causing precipitation of the 2,3,4,5-tetrafluorobenzoic acid. The precipitate can be removed from the aqueous medium by such means as filtration, for example, which is a well known technique. The crystals of the 2,3,4,5-tetrafluorobenzoic acid so obtained contains water and, therefore, retains therein such water-soluble inorganic compounds as ammonium sulfate, though slightly. Removal of the inorganic compounds may be attained simply by washing the crystals with water.

The separation of the 2,3,4,5-tetrafluorobenzoic acid from the aqueous medium may otherwise by attained by extraction from such a solvent as ether or ketone. After the extraction, the solvent entrained by the 2,3,4,5-tetrafluorobenzoic acid can be expelled by evaporation to dryness.

Now, the present invention will be described more specifically below with reference to working examples. It should be noted that this invention is not limited to these examples.

EXAMPLE 1

In an autoclave having an inner volume of 1 liter, 150 g (0.63 mole) of 3,4,5,6-tetrafluorophthalic acid containing no sulfate ion, 8.6 g (0.088 mole) of sulfuric acid, 14.0 g (0.189 mole) of calcium hydroxide, and 500 g of water (after mutual contact within the autoclave, converted to 0.088 mole of calcium sulfate and 0.101 mole of calcium of organic acid, calcium carbonate, or calcium hydroxide in equivalent weight] [pH 1.65 at 70° C. at the time of charging] were placed and then heated and stirred for reaction at 160° C. for 16 hours. The final inner pressure reached 35.5 kg/cm$^2$·G. After completion of the reaction, the reaction mixture was cooled to 70° C. and neutralized with 39.2 g of 30% sulfuric acid and, while kept at 70° C. hot filtered to expel such solids as calcium sulfate. Then, the filtrate was cooled to room temperature. The precipitate consequently formed was separated by filtration, washed with water, and dried, to produce 110.2 g (90.2 mole % in yield based on 3,4,5,6-tetrafluorophthalic acid) of white 2,3,4,5-tetrafluorobenzoic acid.

M.p. 86° to 87° C.

| | Elementary analyses | | |
|---|---|---|---|
| | C (%) | H (%) | F (%) |
| Calculated | 43.30 | 1.03 | 39.18 |
| Found | 43.4 | 1.2 | 39.2 |

By extracting from the filtrate with ether, 7.1 g of 2,3,4,5-tetrafluorobenzoic acid could be further recovered. Calculated from the amount obtained by filtration and the amount obtained by extraction reveals that the present example produced 2,3,4,5-tetrafluorobenzoic acid in a total yield of 96.0 mole % based on 3,4,5,6-tetrafluorophthalic acid.

EXAMPLE 2

Decarboxylation of 150 g of 3,4,5,6-tetrafluorophthalic acid in 500 g of water was effected by following the procedure of Example 1, except that 54.2 g (0.315 mole) of calcium sulfate dihydrate was used as a catalyst and the heating and stirring were carried out at 170° C. for 14 hous [pH 1.37 at 70° C. at the time of charging]. After completion of the reaction, the reaction product was separated by following the procedure, to produce 2,3,4,5-tetrafluorobenzoic acid in a yield of 86.4 mole % as found by the same calculation.

EXAMPLE 3

In an autoclave having an inner volume of 1 liter, 150 g (0.630 mole) of 3,4,5,6-tetrafluorophthalic acid containing no sulfate ion, 29.1 g (0.220 mole) of ammonium sulfate, and 500 g of water were placed and heated and stirred for reaction at 160° C. for 21 hours [pH 1.74 at 30° C. at the time of charging]. After completion of the reaction, the reaction suspension was cooled to room temperature, filtered, washed with water, and then dried, to produce 2,3,4,5-tetrafluorobenzoic acid. Calculation from the amount obtained by filtration and the amount obtained by extraction as in Example 1 reveals that this example produced 2,3,4,5-tetrafluorobenzoic acid in a yield of 85.8 mole %.

EXAMPLE 4

In a flask of an inner volume of 1 liter, 200 g (1.0 mole) of 3,4,5,6-tetrafluorophthalonitrile, 459 g of sulfuric acid, and 391 g of water were placed and heated and stirred for reaction under reflux for 17 hours. After completion of the reaction, the reactant was cooled. The precipitate of 3,4,5,6-tetrafluorophthalic acid consequently formed was separated by filtration. The cake, on analysis, was found to contain 5.0% by weight of sulfuric acid, 2.0% by weight of ammonium sulfate, and 7.2% by weight of water in addition to 3,4,5,6-tetrafluorophthalic acid. In an autoclave having an inner volume of 1 liter, 175 g (150 g as tetrafluorophthalic acid) of a total of 263 g of the cake, 14.0 (0.189 mole) of calcium hydroxide, and 500 g of water were placed and heated and stirred for decarboxylation at 160° C. for 18 hours [pH 1.90 at 70° C. at the time of charging]. The reaction mixture was then treated thereafter by following the procedure of Example 1, to produce white 2,3,4,5-tetrafluorobenzoic acid. By the same calculation as in Example 1, this example was found to have produced 2,3,4,5-tetrafluorobenzoic acid in a yield of 96.4 mole % based on 3,4,5,6-tetrafluorophthalic acid.

EXAMPLE 5

Decarboxylation of 3,4,5,6-tetrafluorophthalic acid was carried out by following the procedure of Example 1, except that the autoclave was provided with a pressure-resistant condenser and a back-pressure valve and the generated carbon dioxide gas was sequentially removed from the system so as to maintain the inner pressure at a fixed level of 6 kg/cm$^2$·G. After completion of the reaction, the reaction product was separated by following the procedure of Example 1. By the same calculation, this example was found to have produced 2,3,4,5-tetrafluorobenzoic acid in a yield of 96.3 mole %.

EXAMPLE 6

Decarboxylation of 3,4,5,6-tetrafluorophthalic acid was carried out by following the procedure of Example 1, except that 238 g (1.00 mole) of 3,4,5,6-tetrafluorophthalic acid, 13.8 g (0.140 mole) of sulfuric acid, 5.5 g (0.042 mole) of ammonium sulfate, 22.2 g (0.30 mole) of calcium hydroxide, and 480 g of water were used [pH 1.89 at 70° C. at the time of charging]. This example was found to have produced 2,3,4,5-tetrafluorobenzoic acid in a yield of 95.4 mole %.

EXAMPLE 7

Decarboxylation of 3,4,5,6-tetrafluorophthalic acid was carried out by following the procedure of Example 1, except that 238 g of 3,4,5,6-tetrafluorophthalic acid, 11.1 g (0.15 mole) of calcium hydroxide, and 480 g of water were used [pH 1.52 at 30° C. at the time of charging]. This example was found to have produced 2,3,4,5-tetrafluorobenzoic acid in a yield of 86.5 mole %.

EXAMPLE 8

Decarboxylation of 3,4,5,6-tetrafluorophthalic acid was carried out by following the procedure of Example 1, except that 238 g of 3,4,5,6-tetrafluorophthalic acid and 480 g of water were used. The reaction product was separated by following the procedure of Example 1 [pH 1.33 at 30° C. at the time of charging]. This example was found to have produced 2,3,4,5-tetrafluorobenzoic acid in a yield of 87.5 mole %.

EXAMPLES 9-15

In Examples 9, 10 and 14, 3,4,5,6-tetrafluorophthalic acid was decarbonated and the decarboxylation products were treated by following the procedure of Example 1, except that catalysts, amount of catalysts, reaction temperatures and reaction times were varied. The results are shown in Table 1. In Examples 11 and 12, 3,4,5,6-tetrafluorophthalic acid was decarbonated and the decarboxylation products were treated by following the procedure of Example 3, except that the decarboxylation products were neutralized by following the procedure of Example 1. The results are shown in Table 1. In Examples 13 and 15, 3,4,5,6-tetrafluorophthalic acid was decarbonated and the decarboxylation products were treated by following the procedure of Example 3, except that catalysts amount of catalysts reaction temperatures and reaction times were varied. The results are shown in Table 1.

TABLE 1

| Example | Catalyst | Amount of catalyst (mole ratio based on TFPA*) | Reaction temperature (°C.) | Reaction time (hours) | TFBA** (mole ratio based on TFPA) |
|---|---|---|---|---|---|
| 9 | CaSO$_4$.2H$_2$O<br>Ca(OH)$_2$ | 0.4<br>0.1 | 160 | 13 | 91.4 |
| 10 | BaSO$_4$<br>BaCO$_3$ | 0.1<br>0.4 | 170 | 20 | 87.5 |
| 11 | Na$_2$SO$_4$<br>NaOH | 0.3<br>0.01 | 140 | 22 | 85.4 |
| 12 | (NH$_4$)$_2$SO$_4$<br>Quinoline | 0.3<br>0.8 | 160 | 18 | 88.8 |
| 13 | K$_2$SO$_4$ | 0.5 | 160 | 12 | 86.7 |
| 14 | CaSO$_4$.2H$_2$O<br>CaF$_2$<br>Ca(OH)$_2$ | 0.2<br>0.04<br>0.08 | 155 | 20 | 93.8 |
| 15 | K$_2$SO$_4$<br>KF | 0.1<br>0.2 | 165 | 20 | 88.3 |

*TFPA: 3,4,5,6-tetrafluorophthalic acid
**TFBA: 2,3,4,5-tetrafluorobenzoic acid

CONTROL 1

In an autoclave having an inner volume of 100 ml, 3.0 g (0.0126 mole) of 3,4,5,6-tetrafluorophthalic acid containing no sulfate ion, 0.5 g (0.0125 mole) of sodium hydroxide, and 50 g of water were placed and heated for reaction at 200° C. for 25 hours. After completion of the reaction, the reaction mixture was cooled to room temperature and extracted with 150 ml of diisopropyl ether. By analyzing this extract by gas chromatography using a 2 m column packed with SE52 and kept at 50° C., the reaction was found to have produced 2.9 mole % of 1,2,3,4-tetrafluorobenzene, 89.1 mole % of trifluorophenol, and substantially no 2,3,4,5-tetrafluorobenzoic acid based on the 3,4,5,6-tetrafluorophthalic acid used as the starting material [pH 2.75 at 25° C. at the time of charging].

CONTROL 2

The procedure of Control 1 was repeated, except that 0.9 g (0.0121 mole) of calcium hydroxide was used in the place of sodium hydroxide and the reaction was carried out at 230° C. for 8 hours. Consequently, there were produced 29.1 mole % of 1,2,3,4-tetrafluorobenzene and 60.3 mole % of trifluorophenol [pH 2.55 at 70° C. at the time of charging].

CONTROL 3

The procedure of Example 1 was repeated, except that 23.4 g (0.316 mole) of calcium hydroxide was used in place of calcium sulfate and the reaction was carried out at 160° C. for 18 hours. Consequently there were obtained 24.7 mole % of 3,4,5,6-tetrafluorophthalic acid, 60.6 mole % of 2,3,4,5-tetrafluorobenzoic acid, and 9.1 mole % of triflurophenol [pH 2.30 at 70° C. at the time of charging].

What is claimed is:

1. A method for the production of 2,3,4,5-tetrafluorobenzoic acid, which comprises effecting said production by decarboxylating 3,4,5,6-tetrafluorophthalic acid in an aqueous medium adjusted to a pH in the range of 0.7 to 2.0 at a temperature in the range of 100° to 195° C. in the presence of at least one compound selected from the group consisting of (a) 0.01 to 0.4 mole of at least one member selected from the group consisting of a hydroxide, a carbonate and or an organic acid salt of an alkaline earth metal, (b) 0.01 to 3.0 mole of a sulfate of at least one member selected from the group consisting of ammonia, an organic base, an alkali metal and an alkaline earth metal, and (c) 0.01 to 3.0 mole of a fluoride of at least one member selected from the group consisting of an alkali metal and an alkaline earth metal per 1 mole of 3,4,5,6-tetrafluorophthalic acid.

2. A method according to claim 1, wherein said pH is in the range of 1.2 to 2.0 and said reaction temperature is in the range of 120° to 180° C.

3. A method according to claim 1, wherein said aqueous medium is 3,4,5,6-tetrafluorophthalic acid containing sulfate ion, obtained by hydrolysis of 3,4,5,6-tetrafluorophthalonitrile with aqueous sulfuric acid solution in the concentration of 30 to 90% by weight at a temperature of 100° to 180° C., which is used for said decarboxylation reaction as is without subjecting the reaction mixture to future purification.

4. A method according to claim 3, wherein said sulfate ion is present in the form of sulfuric acid, ammonium sulfate, or at least one sulfate selected from the group of sulfates of ammonia, alkaline earth metals, alkali metals, and organic bases resulting from neutralization of sulfuric acid.

5. A method according to claim 1, wherein said alkaline earth metal is calcium or barium, said alkali metal is sodium or potassium, said organic base is quinoline or pyridine, and said organic acid salt is 3,4,5,6-tetrafluorophthalate or 2,3,4,5-tetrafluorobenzoate.

6. A method according to claim 1, wherein said 3,4,5,6-tetrafluorophthalic acid is added to the reaction system in an amount of 10 to 200 parts by weight based on 100 parts by weight of said aqueous medium.

7. A method according to claim 1, wherein said aqueous medium is water.

8. A method according to claim 1, wherein the gas generated during the course of said decarboxylation is extracted out of the reaction system so as to keep the pressure in the reaction system in the range of 0 to 15 kg/cm$^2$·G.

9. A method according to claim 1 wherein the amount of the constituents of group (b) is between 0.01 and 1.2 moles thereof.

10. A method according to claim 1 wherein the amount of the constituents of group (c) is between 0.01 and 1.2 moles thereof.

11. A method according to claim 10 wherein the amount of the constituents of group (b) is between 0.01 and 1.2 moles thereof.

12. A method for the production of 2,3,4,5-tetrafluorobenzoic acid, which comprises effecting said production by decarboxylating 3,4,5,6-tetrafluorophthalic acid in an aqueous medium adjusted to a pH in the range of 0.7 to 2.0 at a temperature in the range of 100° to 195° C. in the presence of at least one compound selected from the group consisting of at least one compound selected from the group consisting of an (a) 0.01 to 3.0 mole of a sulfate of at least one member selected from the group consisting of ammonia, an organic base, an alkali metal and an alkaline earth metal, and (b) 0.01 to 3.0 mole of a fluoride of at least one member selected from the group consisting of an alkali metal and an alkali earth metal per 1 mole of 3,4,5,6-tetrafluorophthalic acid.

13. A method according to claim 12 wherein said pH is in the range of 1.2 to 2.0 and said reaction temperature is in the range of 120° to 195°.

14. A method according to claim 12 wherein said alkaline earth metal is calcium or barium, said alkali metal is sodium or potassium, said organic base is quinoline or pyridine, and said organic acid salt is 3,4,5,6-tetrafluorophthalate or 2,3,4,5-tetrafluorobenzoate.

15. A method according to claim 12, wherein said 3,4,5,6-tetrafluorophthalic acid is added to the reaction system in an amount of 10 to 200 parts by weight based on 100 parts by weight of said aqueous medium.

16. A method according to claim 12, wherein said aqueous medium is water.

17. A method according to claim 12, wherein the gas generated during the course of said decarboxylation is extracted out of the reaction system so as to keep the pressure in the reaction system in the range of 0 to 15 kg/cm$^2$·G.

18. A method according to claim 12, wherein said aqueous medium is 3,4,5,6-tetrafluorophthalic acid containing sulfate ion, obtained by hydrolysis of 3,4,5,6-tetrafluorophthalonitrile with aqueous sulfuric acid solution in the concentration of 30 to 90% by weight at a temperature of 100 to 180° C., which is used for said decarboxylation reaction as is without subjecting the reaction mixture to future purification.

19. A method according to claim 12 wherein the amount of the constituents of group (a) is between 0.01 and 1.2 moles thereof.

20. A method according to claim 12 wherein the amount of the constituents of group (b) is between 0.01 and 1.2 moles thereof.

21. A method according to claim 20 wherein the amount of the constituents of group (a) is between 0.01 and 1.2 moles thereof.

* * * * *